(12) United States Patent
Ramsey

(10) Patent No.: US 12,004,923 B2
(45) Date of Patent: Jun. 11, 2024

(54) ACOUSTIC FLUID AND EARPLUG

(71) Applicant: Marc C. Ramsey, Meriden, NH (US)

(72) Inventor: Marc C. Ramsey, Meriden, NH (US)

(*) Notice: Subject to any disclaimer, the term of this patent is extended or adjusted under 35 U.S.C. 154(b) by 0 days.

(21) Appl. No.: 18/460,535

(22) Filed: Sep. 2, 2023

(65) Prior Publication Data

US 2023/0404810 A1 Dec. 21, 2023

Related U.S. Application Data

(63) Continuation of application No. 17/682,109, filed on Feb. 28, 2022.

(60) Provisional application No. 63/304,065, filed on Jan. 28, 2022.

(51) Int. Cl.
*A61F 11/10* (2006.01)
*A61F 11/08* (2006.01)
*G10K 11/162* (2006.01)

(52) U.S. Cl.
CPC ............ *A61F 11/10* (2013.01); *A61F 11/085* (2022.01); *G10K 11/162* (2013.01); *A61F 2250/0003* (2013.01); *A61F 2250/0007* (2013.01)

(58) Field of Classification Search
CPC .................... A61F 11/10; A61F 11/085; A61F 2250/0003; G01K 11/162
See application file for complete search history.

(56) References Cited

U.S. PATENT DOCUMENTS

| | | | |
|---|---|---|---|
| 7,185,655 B1 | 3/2007 | Redon | |
| 10,418,016 B2* | 9/2019 | Goldstein | A61F 11/10 |
| 2008/0264428 A1 | 10/2008 | Purcell et al. | |
| 2009/0214071 A1 | 8/2009 | Axelsson | |
| 2017/0112671 A1* | 4/2017 | Goldstein | H04R 25/554 |
| 2019/0151153 A1* | 5/2019 | Pugliano | B33Y 80/00 |
| 2021/0152911 A1* | 5/2021 | Mizoe | A61F 11/085 |
| 2022/0079813 A1* | 3/2022 | Lawrence | G10K 11/162 |
| 2022/0378619 A1* | 12/2022 | Park | A63B 71/085 |

* cited by examiner

*Primary Examiner* — Jeremy A Luks
(74) *Attorney, Agent, or Firm* — Scale LLP

(57) ABSTRACT

Systems and methods for occluding a duct and attenuating sound may be provided. In some embodiments, a device for attenuating sound passing through a duct or orifice may include a body sized and shaped to be inserted, at least partially, into a duct or orifice. The body may have an interior volume that contains a fluid suspension. In some embodiments, the fluid suspension may include a plurality of gas-filled spheres dispersed in an interstitial fluid. The gas-filled spheres may increase an acoustic attenuation of the fluid suspension relative to the interstitial fluid alone.

14 Claims, 11 Drawing Sheets

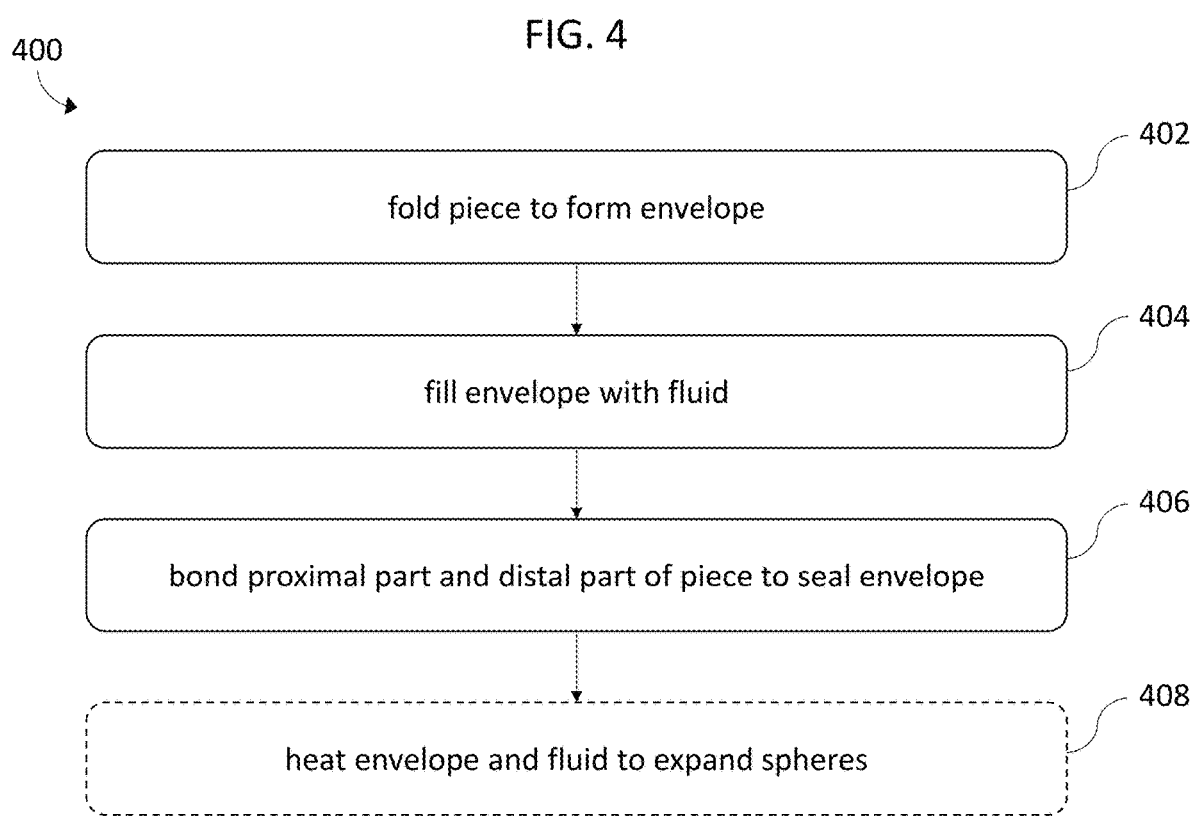

Retracted

Extended

ACOUSTIC FLUID AND EARPLUG

CROSS-REFERENCE TO RELATED APPLICATIONS

This application is a continuation of U.S. patent application Ser. No. 17/682,109, filed Feb. 28, 2022, which claims priority to U.S. Provisional Application No. 63/304,065, filed Jan. 28, 2022. Each of the foregoing are incorporated by reference herein in their entireties.

FIELD OF THE DISCLOSURE

This disclosure relates to devices, compositions, and methods for occluding a duct and attenuating sound. More particularly, this disclosure relates to devices, compositions, and methods of use and manufacture that can be applied to occlude a duct or orifice and attenuate sound passing through the duct or orifice.

BACKGROUND

Noise-Induced Hearing Loss (NIHL) is the most prevalent occupational injury in US industry, affecting more than 10 million workers at a total preventable economic cost of many billions of dollars. US Veterans disability benefits for noise induced hearing loss exceed $1B annually. Globally, 430 million people require rehabilitation services for their hearing loss.

To prevent injury, the United States Occupational Safety and Health Administration (OSHA) standards limit continuous noise exposure to 85 dB SPL over an 8-hour workday, with each additional 5 dB halving the allowable exposure time. 22 million U.S. workers are exposed to workplace noise above these levels and are required to wear hearing protection.

Hearing protectors can offer up to 30 dB of attenuation when worn correctly. However, inexpert wearers in real-world environments generally achieve much less protection with high variability. OSHA therefore requires that all hearing protectors be derated by half. In addition, hearing protection is only effective if it is worn consistently. Noncompliance among workers is high, with primary reasons being discomfort, degraded communication, and interference with job duties.

Single-use "roll-down" ear plugs, made of open-cell elastomer foam, are the most common and effective hearing protection, capable of high attenuation and all-day comfort. However, they are only effective when inserted deeply into the ear canal. This is difficult to achieve except by a motivated and conscientious wearer who has received personalized training. A shallow plug exhibits poor attenuation as well as the "occlusion effect," an amplification of low frequencies and body sounds that leads to poor speech intelligibility. An additional drawback of roll-down plugs is that they do not readily accommodate a pass-through communications channel.

Other types of hearing protection, including muffs and push-to-insert plugs, can be easier to don, but offer either less protection, poorer comfort, or more interference with job functions.

Accordingly, there is a need for systems and methods that can provide improved acoustic attenuation and protection against NIHL. Further, there is a need for systems and methods that can provide improved ease of use and comfort to facilitate compliance, while remaining cost-effective to manufacture.

SUMMARY

The following description presents a simplified summary in order to provide a basic understanding of some aspects described herein. This summary is not an extensive overview of the claimed subject matter. It is intended to neither identify key or critical elements of the claimed subject matter nor delineate the scope thereof.

In some embodiments, a system for occluding a duct or orifice may be provided. In some embodiments, the system may include a toroidal component enclosing an interior volume. In some embodiments, the interior volume may contain a fluid. The toroidal component may have an extended state and a retracted state. When the toroidal component is in the extended state, the interior volume may be disposed between an inner surface and an outer surface of the toroidal component, a distal portion of the toroidal component that defines a distal tip may be configured to extend in a distal direction into an entrance of the duct or orifice, and a proximal portion of the toroidal component defining a proximal end of the toroidal component may configured to extend in a proximal direction opposite the distal direction. When the toroidal component is in the retracted state, a portion of the inner surface may extend proximally beyond the proximal end of the toroidal component.

In some embodiments, a method for occluding a duct or orifice may be provided. In some embodiments, the method may include inserting, at least partially, a toroidal component into the duct or orifice while the toroidal component is in a retracted state. The toroidal component may enclose an interior volume that contains a fluid. In some embodiments, the method may further include transitioning the toroidal component from the retracted state to an extended state. The step of transitioning the toroidal component to the extended state may cause the toroidal component to extend farther into the duct or orifice. In some embodiments, when the toroidal component is in the extended state, the interior volume may be disposed between an inner surface and an outer surface of the toroidal component, a distal portion of the toroidal component that defines a distal tip may be configured to extend in a distal direction into the an entrance of the duct or orifice, and a proximal portion of the toroidal component defining a proximal end of the toroidal component may be configured to extend in a proximal direction opposite the distal direction. When the toroidal component is in the retracted state, a portion of the inner surface may extend proximally beyond the proximal end of the toroidal component.

In some embodiments, a device for attenuating sound passing through a duct or orifice may be provided. In some embodiments, the device may include a body sized and shaped to be inserted, at least partially, into a duct or orifice. The body may include an interior volume that contains a fluid suspension. The fluid suspension may include a plurality of gas-filled spheres dispersed in an interstitial fluid. The gas-filled spheres may increase an acoustic attenuation of the fluid suspension relative to the interstitial fluid alone.

In some embodiments, a method for attenuating sound passing through a duct or orifice may be provided. In some embodiments, the method may include inserting, at least partially, into the duct or orifice a device with an interior volume that contains a fluid suspension. The fluid suspension may include a plurality of gas-filled spheres dispersed in an interstitial fluid. In some embodiments, the gas-filled spheres may increase an acoustic attenuation of the fluid suspension relative to the interstitial fluid alone.

Further variations encompassed within the systems and methods are described in the detailed description of the invention below.

BRIEF DESCRIPTION OF THE DRAWINGS

FIG. 4 shows an exemplary method for manufacturing a fluid-filled component for a sound attenuation device.

FIG. 5A shows the device in a retracted state, and FIG. 5B shows the device in an extended state.

DETAILED DESCRIPTION

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Sound Attenuation Devices, Methods of Use And Manufacture

Figure 1A:
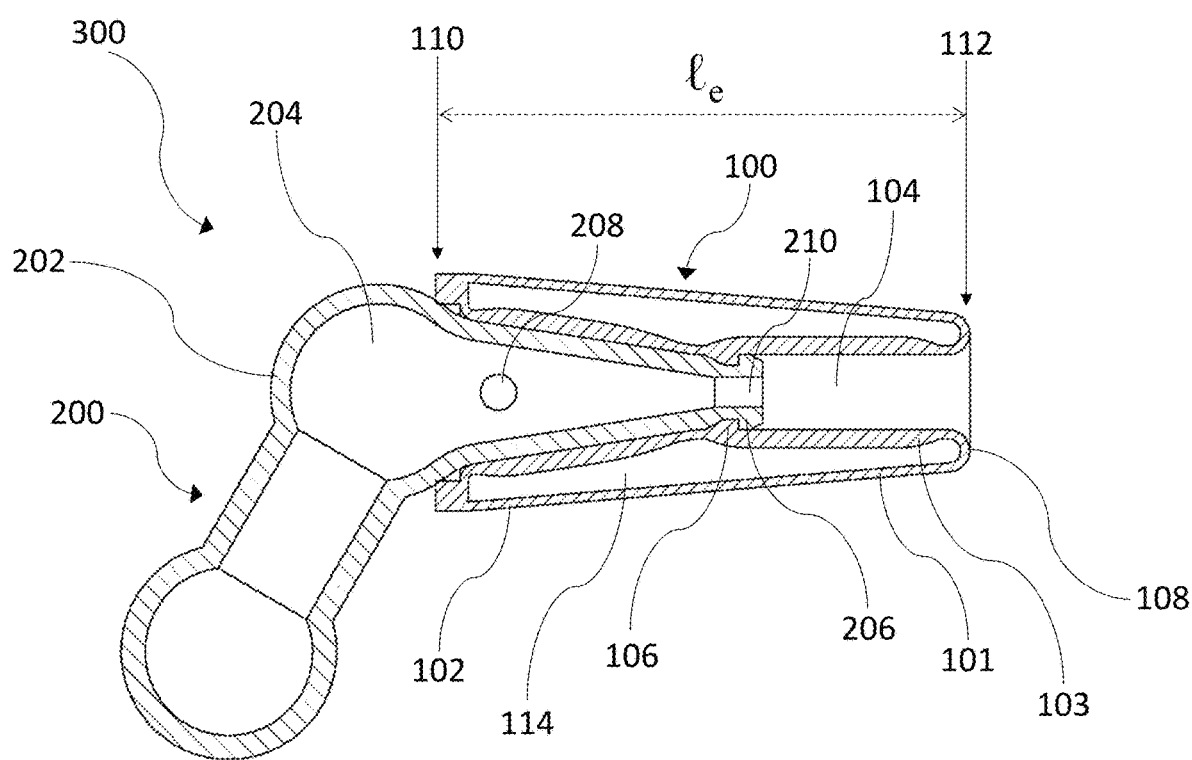
FIG. 1A shows an exemplary sound attenuation device in an extended state.
Figure 1B:
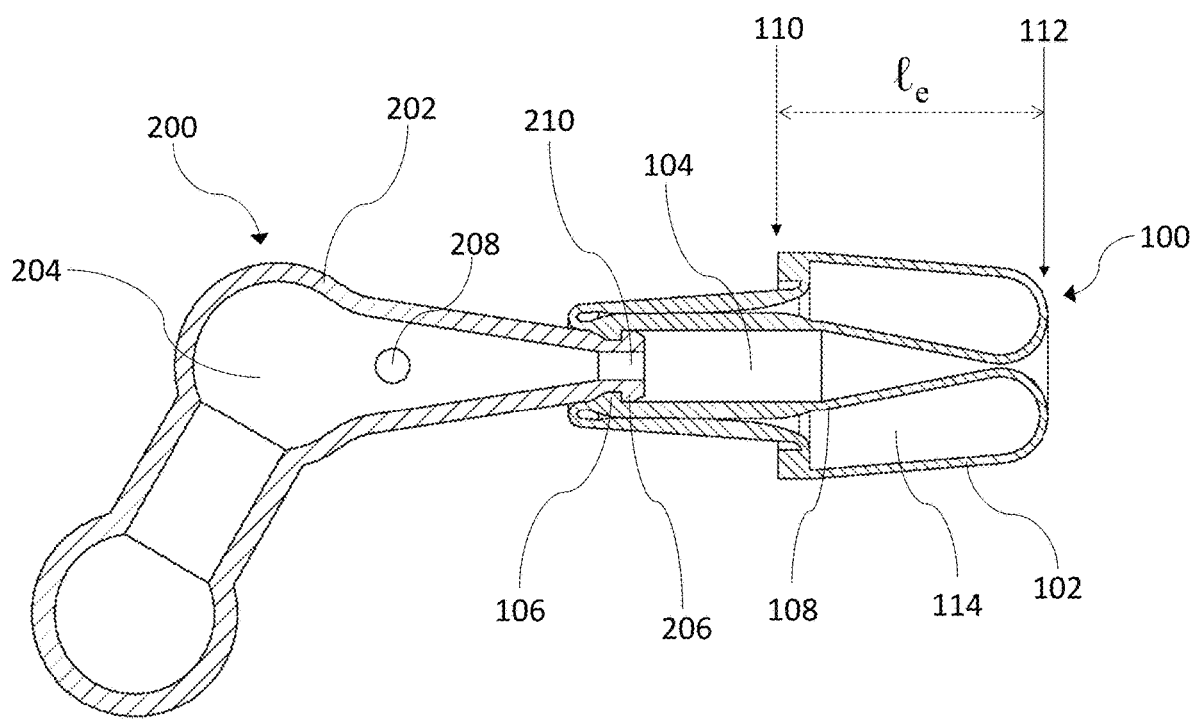
FIG. 1B shows the device of FIG. 1A in a retracted state.

FIGS. 1A and 1B show an exemplary device 300 for attenuating sound in a duct or orifice. The device 300 may be used, for example, to occlude and attenuate sound in a person's ear canal. The device 300 may include a first component 100, which may have a rolling toroidal geometry. In some embodiments, the first component may geometrically stable in at least two states, an extended state (shown in FIG. 1A) and a retracted state (shown in FIG. 1B). The inner and outer surfaces of the first component 100 may be configured to slide relative to one-another such that the first component 100 may transition from the extended state to the retracted state and back. In either the extended state or the retracted state, the first component 100 may be geometrically stable such that it will remain in the selected state in the absence of an external force.

The first component 100 may include a flexible envelope 102, which may wrap around an interior volume 114 in a toroidal geometry. In the extended state, the envelope 102 may define an outer surface 101 and an inner surface 103. The envelope 102 may preferably be molded as a single piece from an elastomer such as silicone. In some embodiments, the envelope may be made from a material with durometer in the range of 20-60 Shore A. In the extended state, the outer surface 101 may face externally away from a central channel 104, and the inner surface 103 may face internally toward the central channel 104. The interior volume 114 may be disposed between the outer surface 101 and inner surface 103 and may be filled with a fluid. As used herein, the term "fluid" encompasses liquids, gases, and suspensions in which substances are dispersed or suspended in a liquid or gas (e.g., flowing powders). In some embodiments, the interior volume 114 may contain one or more fluids such as those described below with respect to FIGS. 8-9.

The first component 100 may have a proximal end 110 and a distalmost portion 112. A distal extent $\ell_e$ of the first component 100 may be defined between the proximal end 110 and the distalmost portion 112. Although the geometry of the first component 100 may change between an extended state (shown in FIG. 1A) and a retracted state (shown in FIG. 1B), the term "proximal end" refers to the portion of the first component that is most proximal when the first component is in the extended state. The term "distalmost portion" refers to the portion of the first component that is most distal at a given time, which may change when the first component transitions between states. For example, as shown in FIG. 1A and FIG. 1B, the distal extent $\ell_e$ of the first component 100 may be greater in the extended state than in the retracted state.

The first component 100 may have a toroidal geometry that surrounds a central channel 104. The central channel 104 may extend axially from the proximal end 110 to the distalmost portion 112 of the first component. A portion 108 of the envelope 102 may define a distal tip 108, which may be at the distalmost portion 112 when the first component is in the extended state, as shown in FIG. 1A. As shown in FIG. 1B, when the first component transitions to the retracted state, the portion 108 may be drawn proximally such that it is disposed within the central channel 104. The first component 100 may also include an engagement structure 106 disposed on an inner surface of the first component 100 along the channel 104. As shown in FIG. 1B, when the first component transitions to the retracted state, the engagement structure 106 may slide proximally such that it extends proximally beyond the proximal end 110 of the first component 100.

In some embodiments, the device 300 may optionally include a second component 200. The second component 200 may have a rigid exterior 202 that surrounds an internal cavity 204. In some embodiments, the second component 200 may be made from a rigid plastic such as nylon, acrylonitrile butadiene styrene, polycarbonate, acrylic, or polyethylene. In other embodiments, the second component 200 may be made from a semi-rigid rubber such as urethane or high durometer silicone. A semi-rigid material may advantageously allow the tip of the second component 200 to deflect slightly as the device 300 is inserted through a bend of an ear canal, increasing comfort.

The cavity 204 may contain air. In some embodiments, the cavity 204 may communicate with an external atmosphere via a vent 208. In some embodiments, the vent 208 may be open when the device 300 is in the retracted state (FIG. 1B) and may be sealed against the envelope 102 of the first component when the device 300 is in the extended state (FIG. 1A). Thus, when the system is in the retracted state, the vent 208 may allow air to travel between the cavity 204 and an external environment, and when the system is in the extended state, the vent 208 may be disposed within the central channel 104 and the envelope 102 of the first component 100 may impede or prevent air from traveling between the cavity 204 and the external environment.

The second component 200 may be sized and shaped such that a portion of the second component 200 extends at least partially into the central channel 104 of the first component 100. Preferably, a portion of the second component 200 remains outside of the central channel 104 of the first component 100, such that a user may grip the second component 200 and apply force to the second component 200 to transition the device 300 between the extended state and the retracted state. Although the second component 200 is shown in FIGS. 1A and 1B with a specific geometry (a tapered section configured to extend into the channel 104, and two bulbs connected by a shaft such that a user may readily grip either of the bulbs to transition the device between states), many alternative geometries may be selected. For example, the second component 200 may include only a single bulb, and the second bulb and connecting shaft may be omitted.

Figure 2:
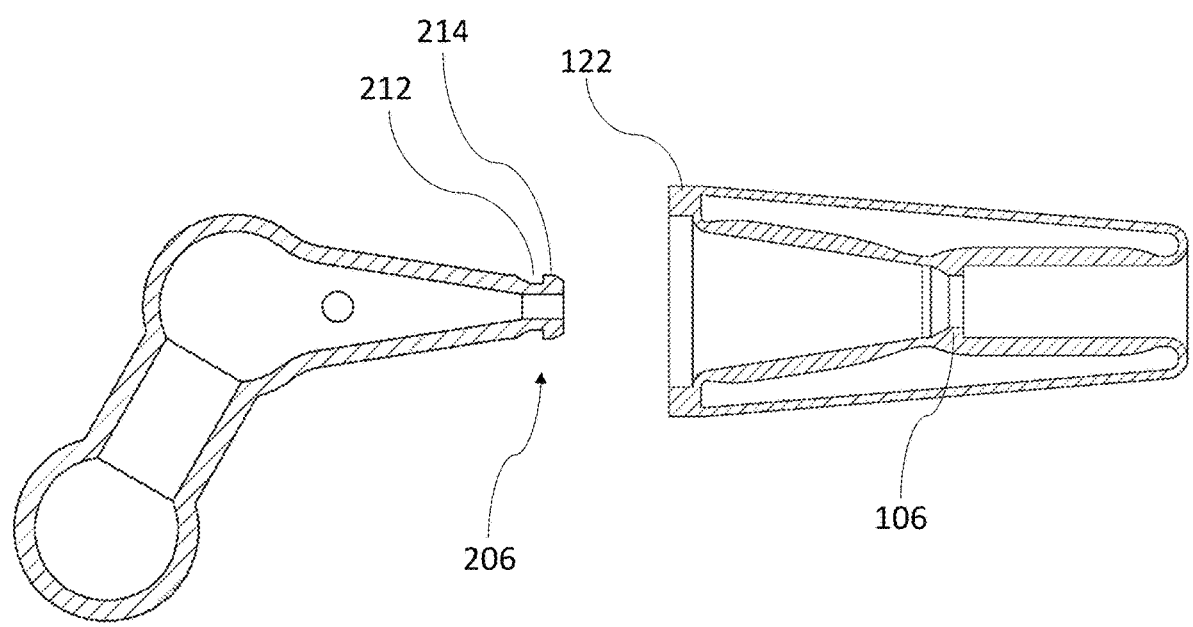
FIG. 2 shows a disassembled state of the components of the device shown in FIGS. 1A-1B.

The second component may include an engagement structure 206, which may be configured to engage the engagement structure 106 of the first component. For example, the engagement structures 106, 206 may have complementary ridges and recesses that are configured to snap fit to one-another. As shown in greater detail in FIG. 2, the second component may have at or near its distal end an annular recess 212 and a head 214. The engagement structure 106 of the first component may include a ridge sized and shaped to extend into the annular recess 212 of the second component. In some embodiments, the distal face of the head 214 and the proximal face of the ridge 106 may have complementary bevels such that the head 214 may slide past the ridge 106, causing the first component 100 to flex outward. When the head 214 is past the ridge 106, the ridge 106 may settle into the recess 212. The proximal wall of the head 214 and the distal face of the ridge 106 may have surfaces that extend at right angles relative to the longitudinal axis of the channel 104, such that opposed faces of the head 214 and ridge 106 resist withdrawal of the second component 200 from the channel 104.

The second component 200 may include an opening 210 at its distal end that communicates with the cavity 204. When the second component 200 is engaged to the channel 104 of the first component 100, the opening 210 may also communicate with the space within the channel 104. When the device 300 is in the extended state, the vent 208 may be sealed against the inner surface 103 of the channel 104, and the channel 104 and the cavity 204 may form a combined sealed air volume that is larger than a volume of the channel 104 alone. This larger combined sealed air volume may beneficially reduce an amplitude of pressure changes in response to a given axial displacement of the system within the duct or orifice. For example, in cases where a plug is inserted into an ear canal, axial displacements of the plug within the canal may cause a pressure within the canal to increase or decrease. Such pressure waves may effectively transmit sound waves across the body of the plug. By increasing the combined air volume, sound transmitted in this manner may be reduced. The larger combined air volume may also reduce uncomfortable pressure differential across the eardrum, thereby increasing a user's comfort when wearing the device 300 and promoting compliance with recommended use.

Figure 3:
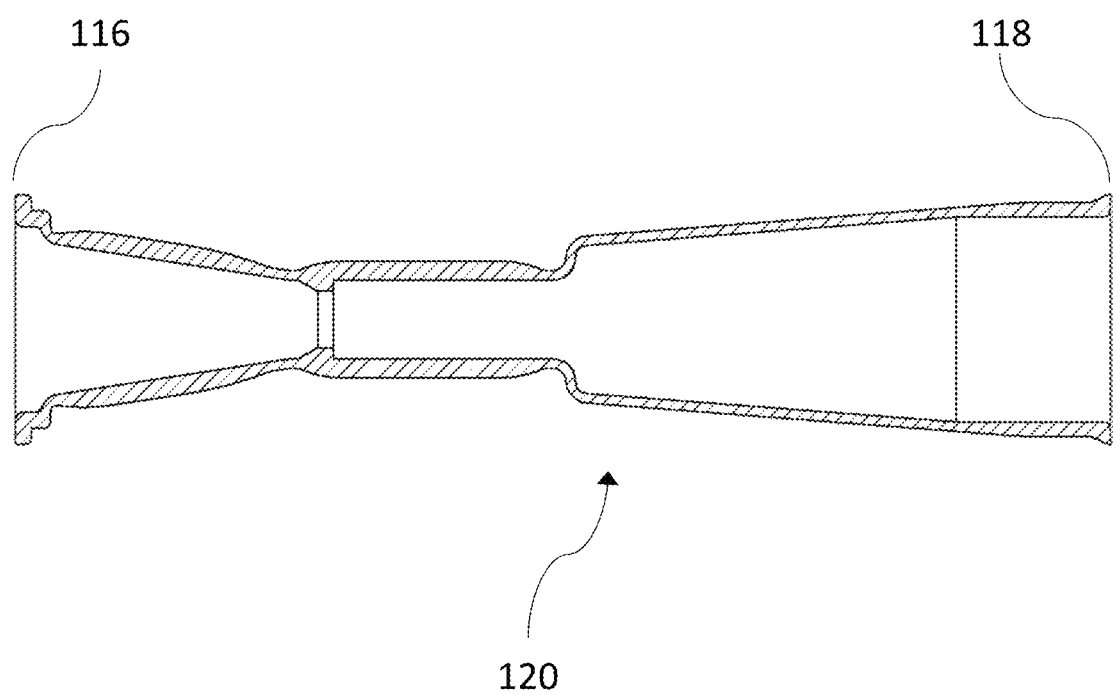
FIG. 3 shows a piece that can be used to form a fluid-filled component such as that shown in FIGS. 1A-1B.

FIG. 3 shows an exemplary piece 120 that can be used to form a toroidal component such as the first component shown in FIGS. 1A-1B. In some embodiments, the piece 120 may be molded as a single integral piece. The piece 120 may be made from any suitable material or combination of materials. In some embodiments, the piece 120 may be made from an elastomer such as silicone. In some embodiments, the piece 120 may be made from a thermoplastic. In some embodiments, the piece may be made from urethane, latex, butyl rubber, neoprene, vinyl, fluoroelastomer, or an elastomeric foam. The piece 120 may have a proximal part 116 and a distal part 118. As described in greater detail below with respect to FIG. 4, the piece 120 may be folded such that the proximal part 116 and distal part 118 may be bonded to one another to form a bond 122 (shown in FIG. 2). For example, the proximal part 116 and distal part 118 may be bonded to one another by applying an adhesive or thermoplastic welding.

FIG. 4 shows an exemplary method 400 for forming a toroidal component such as the first component shown in FIGS. 1A-1B. The method may begin with obtaining a piece such as that shown in FIG. 3. In step 402, a distal end of the piece may be folded at least partially over the length of the piece. In some embodiments, the distal end may be folded over the length of the piece such that the distal end is disposed at or near the proximal end of the piece. Folding the distal end of the piece over the length of the piece may form an envelope with an interior volume disposed between the outer portion of the folded piece and the inner portion of the folded piece. In step 404, the envelope may be filled with a fluid. In some embodiments, the envelope may be filled with a fluid such as those described below with respect to FIGS. 8-9. In some embodiments, the envelope may be only partially filled with a fluid suspension that contains unexpanded spheres. For example, the envelope may be filled with a fluid suspension that occupies less than 70%, less than 50%, or less than 30% of a desired final volume. After the envelope is sealed in step 406, the envelope and fluid suspension may then be heated in optional step 408, which may cause the spheres to expand and the fluid suspension to occupy the desired full volume of the envelope.

In step 406, the proximal part and distal part of the piece may be bonded to one-another to seal the envelope and enclose the fluid. For example, an adhesive may be applied and set, or heat may be applied to weld the proximal part and the distal part together.

Figure 5A:
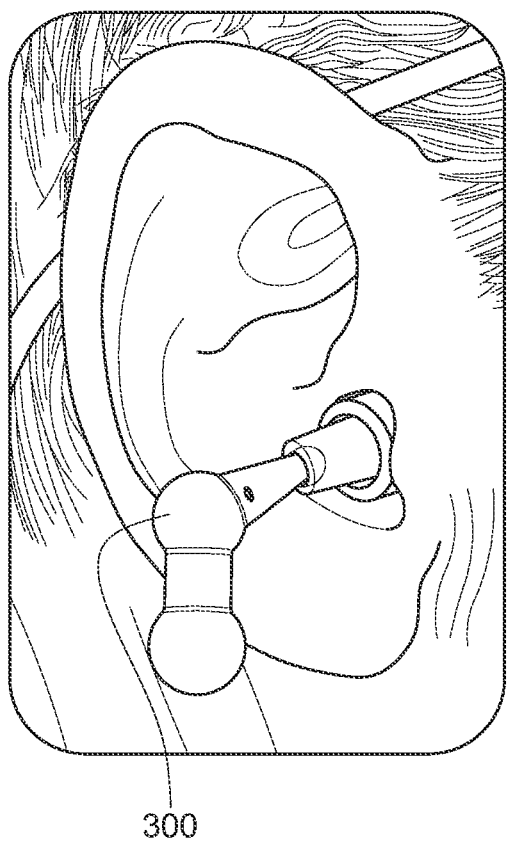
FIGS. 5A and 5B show an exemplary sound attenuation device inserted in an ear.
Figure 5B:
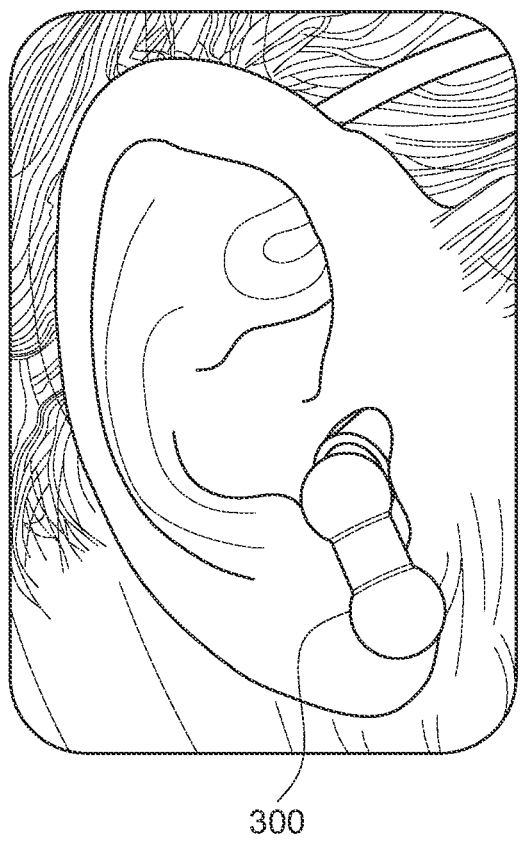

FIGS. 5A and 5B show the device 300 in a person's ear canal. FIG. 5A shows the device 300 in a retracted state (e.g., a state shown such as that shown in FIG. 1B), and FIG. 5B shows the device 300 in an extended state (e.g., a state such as that shown in FIG. 1A).

Figure 6:
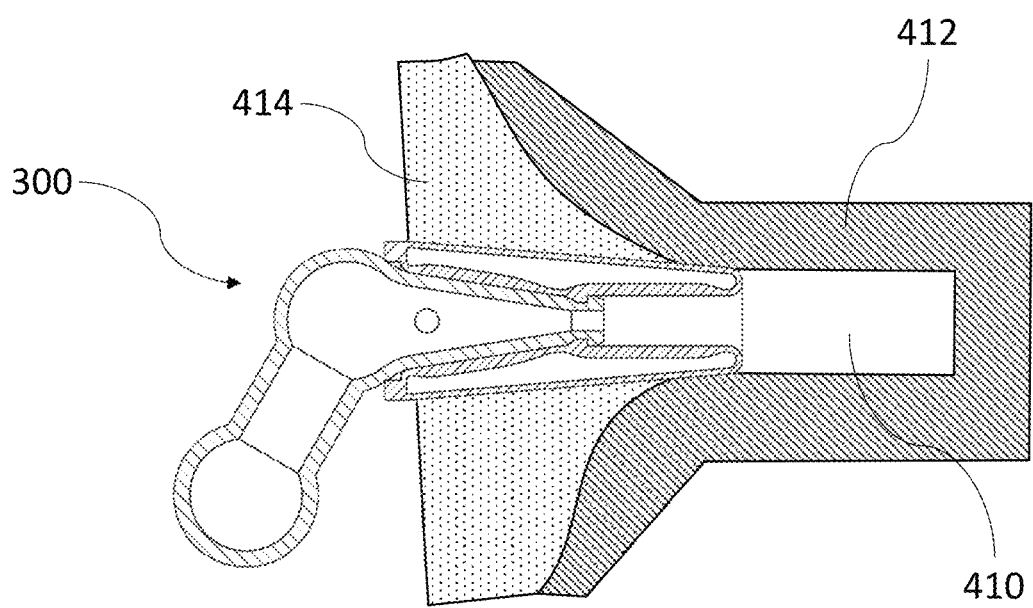
FIG. 6 shows a sound attenuation device inserted into a bony portion of an ear canal.

FIG. 6 is a cross-sectional diagram showing how a device 300 may extend into the anatomy of a person's ear canal 410. An outer portion of a human ear canal 410 is surrounded by soft tissue 414, and an inner portion of the ear canal 410 closer to the eardrum is surrounded by bony tissue 412. The soft tissue 414 can vibrate when struck by sound waves, which can transmit sound around an earplug that is not inserted sufficiently far into the canal 410. These vibrations are only minimally transmitted to the bony tissue 412, and the bony tissue 412 therefore conveys very little sound into the ear canal. By inserting the device 300 so that it extends at least partially into the portion of the ear canal 410 that is surrounded by bony tissue 412, the device 300 can reduce the amount of sound that travels around the device 300 and to the eardrum.

Figure 7:
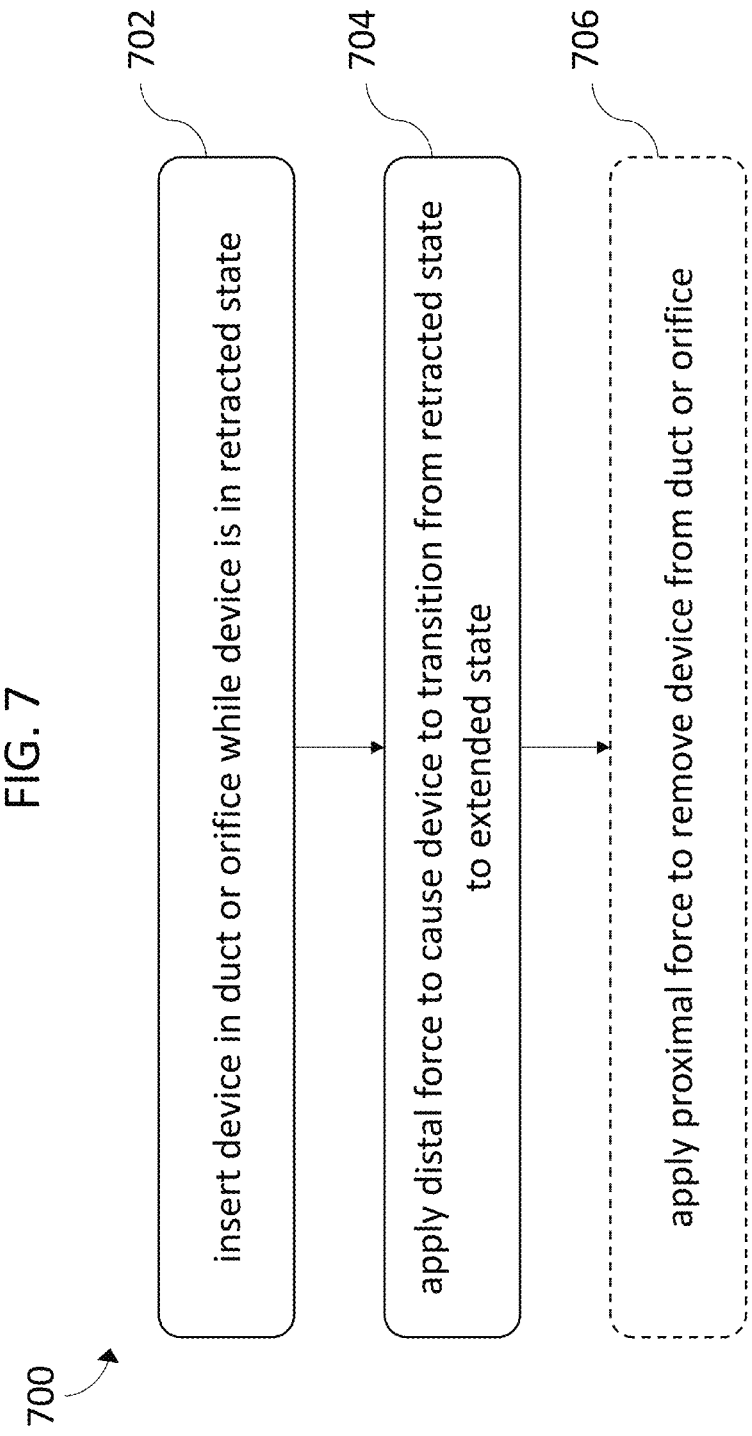
FIG. 7 shows an exemplary method for occluding a duct or orifice.

FIG. 7 shows an exemplary method 700 for occluding a duct or orifice. In step 702, a device, such as device 300 shown in FIGS. 1A-1B, may initially be inserted into the duct or orifice in a retracted state (e.g., a retracted state such as shown in FIGS. 1B and 5A). In some embodiments, the duct or orifice may be an ear canal. In some embodiments, when the device is inserted in the retracted state, the distal tip of the first component 100 of the device 300 may be disposed within a portion of an ear canal that is surrounded by soft tissue. In step 704, the user may apply a distally directed force to the device. For example, the user may apply a distally directed force to a second component such as that shown in FIGS. 1A-1B, which may cause the device to transition from the retracted state (e.g., FIG. 1B) to an extended state (e.g., FIG. 1A). In some embodiments, the transition may cause the distal tip to advance further into the duct or orifice. In some embodiments, the distal tip may advance further into the duct or orifice while an outer surface of the device remains engaged with and, optionally, stationary relative to an inner surface of the duct or orifice.

In the extended state, after step 704 is performed, the distal tip of the device may be disposed in a portion of an ear canal that is surrounded by bony tissue. In some embodiments, step 704 may also cause a vent in the second component to advance into and seal against a channel of the first component, producing a combined sealed air volume that includes a portion of the ear canal, a channel within the ear canal, and a cavity within the second component. In some embodiments, the vent may allow air to escape as the device advances into the canal, but may be automatically sealed by the body just as the plug seats into its final position. This may advantageously prevent uncomfortable pressure from being produced in the canal during insertion. By first inserting the device in the retracted state and then transitioning the device to an extended state, a deep insertion of the device into an ear canal can be easily and repeatedly accomplished, even by untrained users. This may promote better compliance and more assured protection against noise-induced hearing loss.

In optional step 706, the device may be removed by applying a proximal force to the device. In some embodiments, the proximal force may be applied to the second component, which may transmit the proximal force to the first component via an engagement structure between the first component and the second component. In some embodiments, applying the proximal force may cause the device to transition back to the retracted state while the device is being removed from the duct or orifice.

The devices and methods described above with respect to FIGS. 1-7 provide several advantages. The device 300 may be configured such that it may advance into an ear canal without friction and form a low-pressure, large-area seal deep in the canal. Relative to a solid or foam earplug, a fluid-filled device 300 may provide benefits such as improved flexibility, sound attenuation, comfort, and the ability to transition states to extend deeply into an ear canal.

Meanwhile, the devices described herein avoid the need for inflation, pumps, valves, or significant pressure and material strain. Earplugs with inflation mechanisms suffer from several mechanical deficiencies. First, as a balloon inflates, the outer membrane must be placed under tension and strain, generally taking on a nominally cylindrical or spherical shape. Such a taught, smooth membrane does not readily seal against the irregular surface of the inner ear canal unless significant additional internal pressure is applied. Second, in order to limit the required inflation pressure to a reasonable value, the inflatable balloon must be made with a very thin wall and very soft material. This makes it fragile. Third, if the balloon membrane does rupture while pressurized within the ear, it can propel pressurized fluid and gas into the ear canal. This can lead to a disturbing acoustic sensation, an unpleasant mess, and possibly even damage to the eardrum. Finally, the relatively high pressure required to form a seal can cause discomfort in the ear canal even under ideal conditions. Further, it can be problematic to fold the membrane because folds can introduce leak paths that make sealing difficult.

A fluid-filled device that avoids the need for an inflation mechanism can employ a thicker, stronger elastomer envelope while still providing higher compliance, better comfort, and a more reliable seal.

The embodiments described herein may enable a low-pressure, conformable, large-area seal to be formed deep in the ear canal. The devices may be slightly oversized (in a nominal state) relative to an ear canal. Thus, unlike an inflatable earplug in which the sealing surface is expanded and taught, in some embodiments of device 300, the sealing surface may be in slight compression. As a result, the sealing surface of the device can easily conform to the peaks and valleys of the irregular ear canal surface under the influence of only slight internal pressure. Membrane tension need not be overcome in order to allow the surface to extend into the valleys.

The total fluid volume of fluid in the device may remain constant and need not flow through narrow channels or constrictions. The fluid therefore need not be exposed to high strain rate or significant pressure, and an elastomer that makes up the body envelope may avoid being placed under significant strain. This may beneficially lead to minimal fatigue and long life. In some embodiments, the device can be used repeatedly for months or years.

The device may include a robust elastomer envelope that can be readily cleaned with a cloth and/or solvent. When retracted, the portion of the envelope that advances deep into the ear canal may be protected within the central channel, unexposed to the wearer's fingers. This may protect against contamination being introduced to the surface and subsequently transferred deep into the ear canal. In some embodiments, the first component and second component can be separated by applying sufficient force. For example, with reference to the embodiment shown in FIG. 2, when a user applies sufficient force (e.g., a force that is greater than the force used to transition the device from the extended state to the retracted state), the head 214 may cause the ridge 106 and the envelope to elastically deform such that the head 214 may be pulled proximally past the ridge 106 and removed from the channel. By separating the first component and the second component, the respective components may readily be cleaned or replaced and then snapped back together.

Because the fluid does not need to flow through any constriction, pump, or valve, a very high viscosity fluid can be used, leading to high acoustic attenuation. In other embodiments, the device can be filled with a high-molecular weight gas, which may improve the acoustic properties of the device relative to environmental air or gases such as nitrogen. For example, in some embodiments, the device may be filled with sulfur hexafluoride.

Embodiments of the devices described above may naturally accommodate a large diameter isolated acoustic pass-through coupled to a sealed air volume within the first and second components. These features serve at least two purposes. First, this makes the total sealed air volume between the device and eardrum much larger than with a traditional earplug. This may reduce low frequency sound transmission by reducing the amplitude of pressure changes in response to a given axial displacement of the earplug. Second, communications electronics or acoustic filters can be conveniently incorporated into the device (e.g., in the second component) and communicate directly with the eardrum, without a long narrow channel in between that can distort sound.

Because the fluid need not be under significant pressure when the device is inserted, the envelope is unlikely to rupture. If the envelope does rupture, it will not project fluid with any significant force. Moreover, because there is no need for a separate reservoir, pump, diaphragm, or valve, the device is much simpler and more compact than an inflatable earplug.

When the device is inserted, the second component may be securely anchored deep in the channel of the first component and the ear canal. This may produce a secure and stable fit even if the second component is fitted with a significant mass of communications electronics and the wearer engages in strenuous activity such as running.

Although much of the description above considers the use of devices to occlude and attenuate sound in a human ear, embodiments of the devices described herein may be used in other acoustic sealing applications, such as to occlude non-human ear canals or to reduce sound traveling through other orifices, such as in machinery or construction applications.

Accoustic Attenuation Compositions

Most fluid-filled earplugs suffer from a common acoustic deficiency. A heavy, incompressible liquid volume anchored to the ear canal by an elastic membrane forms a resonator that oscillates axially within the ear canal like a piston. This can be loosely analogized to a water balloon disposed in a pipe—if the pipe were shaken axially, the balloon would oscillate back and forth. This motion alternately compresses and expands (or "pumps") the volume of air sealed between the earplug and eardrum, generating pressure fluctuations that effectively transmit or even amplify low frequency sound.

Sound waves are pressure disturbances that propagate through a medium. A sound wave can be characterized by its frequency, wavelength, and amplitude. Amplitude can be quantified in terms of either pressure, particle velocity, or displacement. Sound waves relevant to hearing have frequency in the range of 100-20,000 Hz.

Acoustic media have several key properties that define the relationships between the pressure, particle velocity, and displacement of a sound wave. The most basic properties are density and sound speed.

Sound speed in a medium is related to the ratio of the bulk elastic modulus (i.e., the reciprocal of compressibility) to density. Dense, compressible media have low sound speed, while lower density, less compressible media have higher sound speed. Typical liquids have sound speed in the range of 1000-2000 m/s, while atmospheric air has a sound speed of about 340 m/s.

A third property of acoustic media is acoustic impedance, defined as the ratio of the pressure amplitude to the particle velocity, and calculated as the product of density and sound speed. Low density, compressible media (like air) have low impedance, while dense, incompressible media (like pure liquids and solids) have high impedance. At a boundary between two media with differing impedance, sound waves are partially reflected and partially transmitted. If their impedances are similar, most of the energy is transmitted. If they are different, most is reflected.

Another property of acoustic media is the attenuation coefficient, which describes the rate at which acoustic energy is lost as a wave propagates. Pure gasses, liquids, and solids generally have very low attenuation in the audible frequency range. Inhomogeneous media such as suspensions and foams can have much higher attenuation.

Adding gas bubbles to a liquid dramatically increases its compressibility while only modestly decreasing its density. Consequently, a liquid with gas bubbles at a volume fraction of 0.4-0.6 has a sound speed of only 20 m/s, lower than the pure liquid by a factor of 100. Combined with the decrease in density, this represents an acoustic impedance lowered by a factor of 200. This very low acoustic impedance leads to very high acoustic particle velocities and displacements.

A basic resonator consists of a mass, spring, and damper. When the mass is perturbed, it oscillates back and forth on the spring until the energy is absorbed by the damper. The frequency is related to the ratio of spring constant to mass. A large mass or weak spring leads to low frequency, while a smaller mass or stronger spring leads to higher frequency. Damping determines how quickly energy is absorbed. Damping generally has a small effect on the amplitude of the first oscillation, but strongly determines the length of time that the resonator will oscillate (or "ring") before the perturbation dies out. This decay time is related to a parameter known as the damping ratio, which includes the inertial effects of the mass. Lower mass leads to higher damping ratio and faster decay.

Viscosity refers to the tendency of a fluid to resist shear strain. For example, water has low viscosity; honey has high viscosity. The viscosity of a liquid can be increased by adding rigid particles in suspension. This is because the particles must rub together with only a thin layer of liquid between them, increasing the microscopic stain rate generated at a given macroscopic strain rate. Adding monodisperse rigid spheres at a volume fraction of around 0.6 increases viscosity by a factor of ten. This relationship does not apply to bubbly liquids. Because gas bubbles are not rigid, bubbly liquids generally have low viscosity.

Fluid-filled earplugs using incompressible liquids or suspensions present significant drawbacks. These fluids have very high acoustic impedance compared to air. High frequency sound, which has short wavelength, is strongly reflected from these earplugs. However, low frequency sound has wavelength much longer than the dimensions of the physical earplug. As a result, these frequencies do not couple acoustically into the liquid itself. Instead, the earplug fluid moves as a rigid body in response to the pressure applied by the sound, like a fishing bobber on an ocean wave. This causes the earplug to act like a resonator. The dense fluid provides a large mass while the elastic membrane provides a weak spring, causing the earplug to resonate at low frequencies and respond strongly to these sound waves. Fluid viscosity can help damp this resonator, but even small displacements of the earplug "piston" cause significant pressure fluctuations in the air volume sealed within the ear canal. Viscosity alone cannot provide sufficient damping.

With these considerations in mind, novel acoustic attenuation fluids are described. Such fluids may be used in fluid-filled sound attenuation devices, including but not limited to those described above with respect to FIGS. 1-7.

Figure 8:
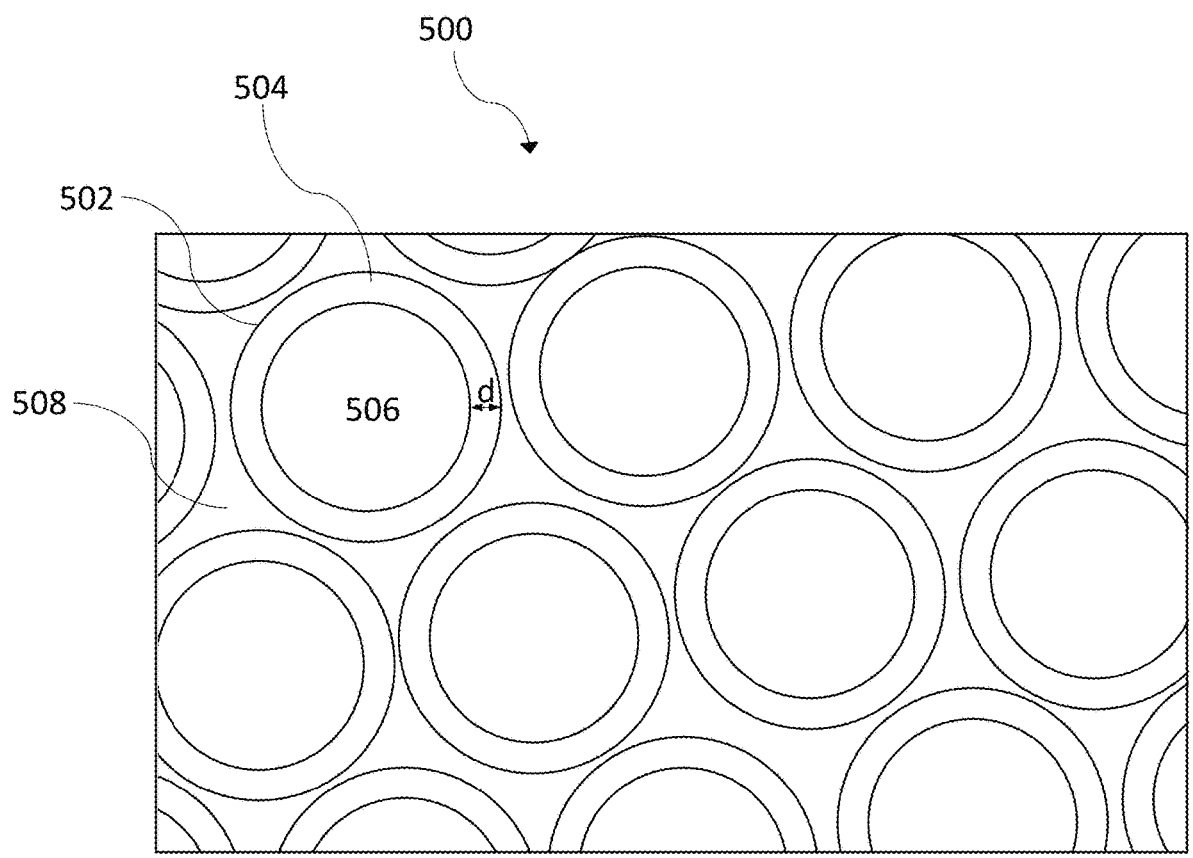
FIG. 8 shows an exemplary composition for attenuating sound.

FIG. 8 shows an exemplary acoustic attenuation fluid 500. In some embodiments, the fluid 500 may be a suspension that includes an interstitial fluid 508 and a plurality of spheres 502.

In some embodiments, the interstitial fluid 508 may be inert and non-toxic in humans and may have a viscosity in the range of 0.1-10 Pa·s. In some embodiments, the interstitial fluid 508 may have a viscosity in the range of 0.0001-0.01 Pa·s, 0.01-1 Pa·s, or 1-100 Pa·s. The interstitial fluid 508 may preferably have high molecular weight, which may limit diffusion of the liquid through a wall of a sound attenuation device and through the shells 504 of the spheres 502. The interstitial fluid 508 may have vapor pressure below 0.1 mmHg. A vapor pressure in this range may advantageously limit evaporation that could otherwise cause a sound attenuation device to dry out over time. In some embodiments, the interstitial fluid 508 may be a liquid, emulsion, or solution. For example, the interstitial fluid 508 may include mineral oil, glycerin, silicone oil, or other suitable liquids.

In other embodiments, the interstitial fluid 508 may be a gas, and the plurality of spheres 502 may flow as a dry powder. In such embodiments, the fluid suspension 500 may have non-linear viscosity and acoustic properties.

One or more of the spheres 502 may have a shell 504 that encloses an interior volume 506. In some embodiments, one or more of the shells 504 may have a wall thickness d that is between 0.01-1,000 microns. In some embodiments, the wall thickness may be in the range of 0.05-100 microns, 0.1-10 microns, or 1-5 microns. For acoustic applications other than earplugs, larger, thicker-walled spheres may be used. In some embodiments, the spheres 502 may have diameters in the range of 1 micron to 2 millimeters. In some embodiments, the spheres 502 may have a diameter in the range of 1-500 microns, 5-100 microns, or 20-70 microns. The ratio of diameter to wall thickness may preferably be greater than 50, greater than 20, or greater than 10. In some embodiments, the shell 504 may be made from a material with an elastic modulus in the range of 0.1-5 GPa. In some embodiments, the shell may be made from a thermoplastic polymer such as a co-polymer of acrylonitrile.

In some embodiments, the interior volume 506 may contain a gas. In some embodiments, the gas may be atmospheric air or other chemically stable gases such as nitrogen. In some embodiments, the interior volume 506 may contain a gas with a relatively high molecular weight such as sulfur hexafluoride. In some embodiments, the spheres 502 may contain a gas with a molecular weight of at least 100 g/mol.

In some embodiments, the fluid suspension 500 may contain spheres 502 having homogenous size, wall thickness, interior volumes, and material properties. In other embodiments, the characteristics of the spheres 502 in the fluid suspension 500 may be varied. The spheres 502 may preferably be resiliently compressible, such that when a force is applied, the shells 504 may bend inwardly and compress the gas in the interior volume 506, and when the force is removed, the spheres 502 may return to their spherical states.

In some embodiments, the plurality of spheres 502 may occupy a volume fraction of the fluid suspension 500 that is between 0.1-0.99 when the fluid suspension is at atmospheric pressure. In some embodiments, the volume fraction may be between 0.2-0.9, 0.4-0.7, or 0.5-0.6. In some embodiments, the spheres 502 may be evenly distributed in the fluid suspension 500. In some embodiments, the viscosity of the mixture may be in the range of 1-100 Pa·s or 5-20 Pa·s.

Exemplary spheres are commercially available and are marketed as a filler or blowing agent. These commercially available spheres have not previously been proposed for use in liquids to improve noise attenuation. The spheres can be supplied un-expanded or expanded, dry or wet. Un-expanded spheres can be expanded with heat during a fabrication process.

In some embodiments, a fluid suspension with small, thin-walled, high elastic modulus, gas-filled spheres dispersed in an interstitial fluid, such as those described above, may essentially form a fluid foam that is stable, compressible, low density, and high viscosity. It may also exhibit a non-linear bulk modulus, with high compressibility but lower expansibility. This is due to the high elastic modulus, thin-walled spheres, which can compress by crumpling, but resist expansion.

These compositions provide several properties that combine to improve the acoustic attenuation of a fluid-filled device compared to an incompressible liquid or suspension. For example, these compositions may provide lower density, lower sound speed, and higher compressibility while still providing very high viscosity. This combination of properties leads to several benefits, certain of which are described below.

First, the lower density decreases the total mass of a fluid an sound attenuation device. This increases both the resonant frequency of the device and its damping ratio, reducing its oscillatory response at low frequencies.

Second, the high compressibility and low density lead to very low sound speed as well as acoustic impedance that is extremely low compared to pure liquids, but still considerably higher than air. The impedance mismatch with air means that most airborne sound may be reflected. However, the sound that is transmitted into the fluid moves very slowly (with wavelength reduced substantially, such as by a factor of approximately 100) and generates very high acoustic particle velocities and displacements. This means that very low frequencies can couple directly into the fluid and interact strongly with it.

Finally, the high-modulus shells allow the gas-filled spheres to be compressible but still to act like rigid particles when in shear. This leads to high viscosity. High acoustic particle velocities and displacements combined with high viscosity lead to extremely high acoustic attenuation. The non-linear bulk modulus of the fluid may further increase this attenuation.

When a fluid suspension 500 is used to fill a sound attenuation device, the device may advantageously not act like a rigid-body resonator piston that can transmit or amplify sound but may instead absorb and dissipate the sound. This may significantly reduce the amount of sound that reaches a distal part of the sound attenuation device and, in the case where the device is inserted in an ear canal, may significantly reduce the amount of sound that reaches the ear drum.

Exemplary acoustic attenuation fluids may be stable fluid foams with unique physical and acoustic properties. These fluids may be used in a wide range of applications that can benefit from a fluid (rather than a solid or elastomer) that provides acoustic, thermal, or mechanical isolation. Specific examples may include a variety of hearing protection devices, acoustic diagnostic devices, thermal insulation, and many others.

Figure 9:
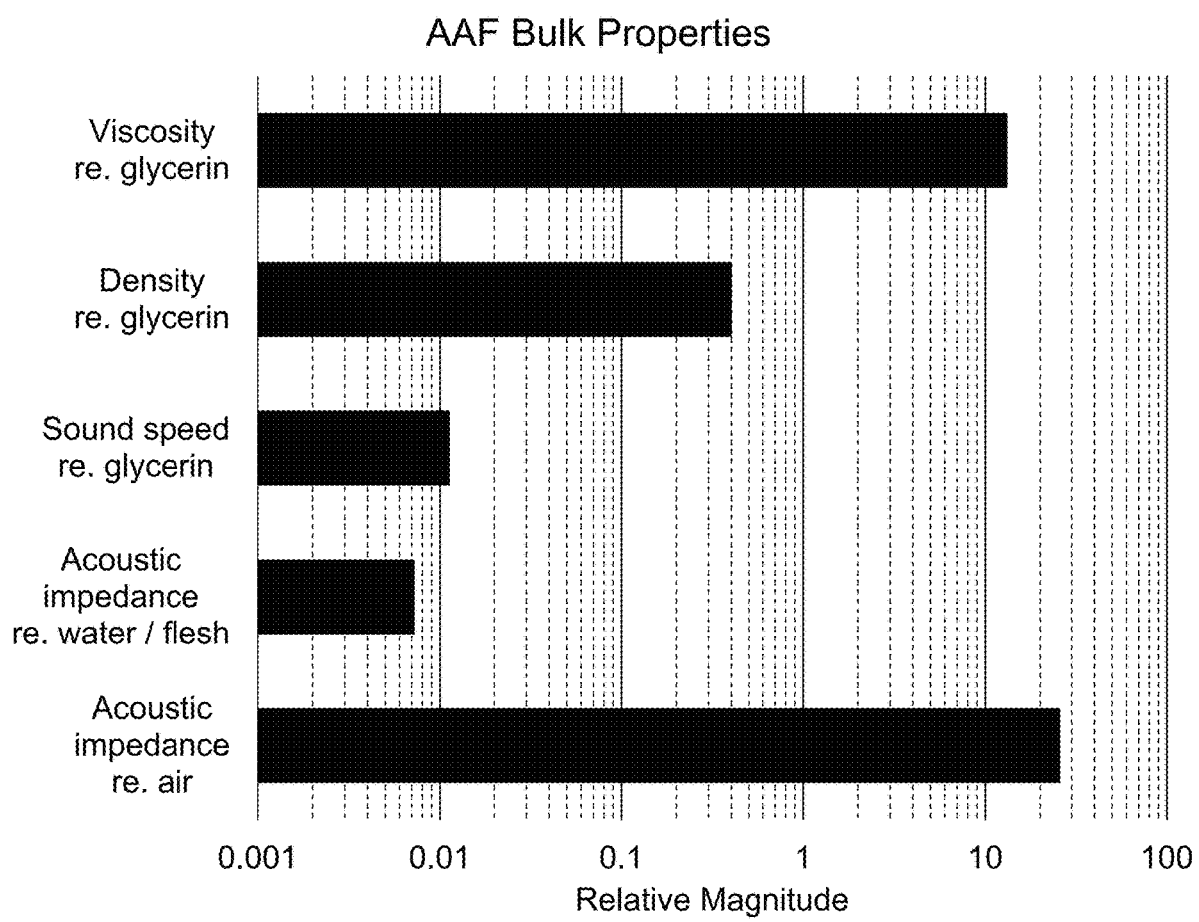
FIG. 9 shows bulk physical properties for an exemplary composition.

FIG. 9 shows calculated bulk properties of an exemplary acoustic attenuation fluid (AAF) that includes an interstitial fluid and a plurality of gas-filled spheres as described above relative to other media. As shown in FIG. 9, an exemplary AAF may have acoustic impedance more than two orders of magnitude below that of water or fleshy tissue and more than an order of magnitude greater than air. For example, the exemplary AAF may have an acoustic impedance that is less than 5%, less than 1%, less than 0.5%, or less than 0.1% that of water. The exemplary AAF may also have an acoustic impedance that is at least 2 times, at least five times, or at least 10 times that of air. Thus, the exemplary AAF may present a large impedance discontinuity at interfaces with either of these media, resulting in strong acoustic reflection. The AAF may also present viscosity more than an order of magnitude greater than glycerin. For example, the exemplary AAF may present a viscosity that is at least 2 times, at least 5 times, or at least 10 times that of glycerin. The low acoustic impedance and high viscosity of the AAF lead to very high acoustic attenuation compared to glycerin and other pure liquids.

Figure 10:
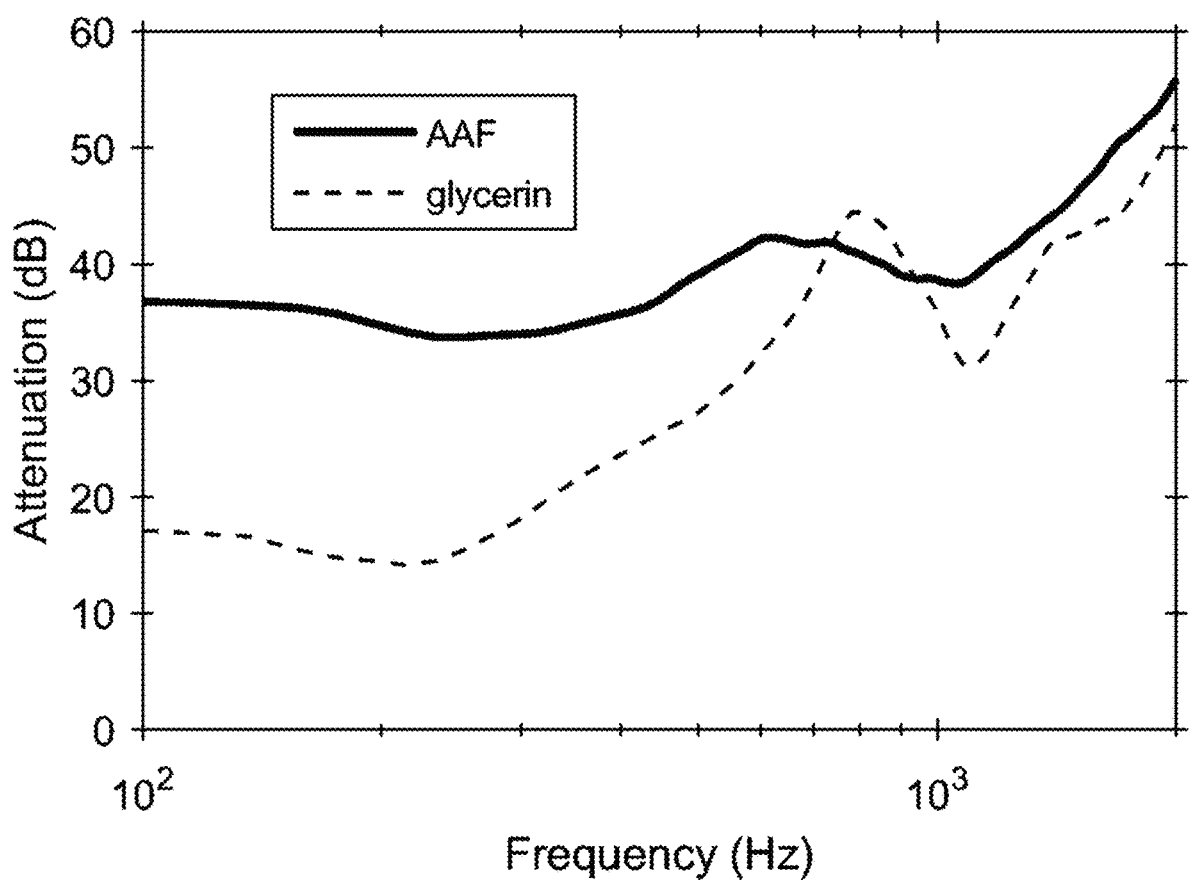
FIG. 10 shows measured sound attenuation for an exemplary device filled with an exemplary composition compared to the same device filled with a pure liquid.

FIG. 10 shows the low frequency attenuation of a fluid-filled earplug filled AAF compared to an identical earplug filled with glycerin as measured in a laboratory ear simulator. The earplug filled with AAF provides substantially greater attenuation than does the earplug filled with glycerin at frequencies below about 800 Hz. For example, at a frequency of 125 Hz, an earplug filled with AAF may provide improved attenuation, relative to an identical earplug (subject to manufacturing tolerances) filled with glycerin, of at least 3 dB, at least 6 dB, at least 9 dB, at least 12 dB, at least 15 dB, or at least 18 dB. In some embodiments the improved attenuation at a frequency of 125 Hz may be between 6-21 dB, between 9-18 dB, or between 12-18 dB.

NUMBERED EMBODIMENTS

The numbered embodiments below describe exemplary combinations of features disclosed throughout this detailed description.

A1. A system for occluding a duct or orifice, the system comprising:
   a toroidal component enclosing an interior volume, the interior volume containing a fluid;
   the toroidal component having an extended state and a retracted state;
   wherein:
      when the toroidal component is in the extended state:
         the interior volume is disposed between an inner surface and an outer surface of the toroidal component;
         a distal portion of the toroidal component that defines a distal tip is configured to extend in a distal direction into an entrance of the duct or orifice; and
         a proximal portion of the toroidal component defining a proximal end of the toroidal component is configured to extend in a proximal direction opposite the distal direction; and
      when the toroidal component is in the retracted state, a portion of the inner surface extends proximally beyond the proximal end of the toroidal component.

A2. The system of embodiment A1, wherein the toroidal component has a central channel, the portion of the inner surface being disposed within the central channel when the toroidal component is in the extended state.

A3. The system of embodiment A2, further comprising a second component, the second component extending at least partially within the central channel and engaging the portion of the inner surface.

A4. The system of embodiment A3, wherein the portion of the inner surface comprises a structure to which the second component snap-fits and engages.

A5. The system of any of embodiments A3-A4, wherein the second component comprises an air cavity and a vent, wherein:
   when the system is in the retracted state, the vent allows air to travel between the air cavity and an external environment; and
   when the system is in the extended state, the vent is disposed within the central channel.

A6. The system of embodiment A5, wherein the second component has an opening at its distal end that communicates with the central channel of the toroidal component such that, when the system is in the extended state, the central channel of the toroidal component and the air cavity of the second component form a combined sealed air volume that is larger than a volume of the central channel alone, the larger combined sealed air volume reducing an amplitude of pressure changes in response to a given axial displacement of the system within the duct or orifice.

A7. The system of any of embodiments A3-A6, wherein the system is configured such that, upon inserting the toroidal component into the duct or orifice while the system is in the retracted state, pressing the second component in the distal direction causes the system to transition from the retracted state to the extended state.

A8. The system of any of embodiments A2-A7, wherein, when the system is in the retracted state, the distal portion of the toroidal component is drawn proximally into the central channel, such that a distal extent of the toroidal component measured from the proximal end to a distalmost portion of the toroidal component is shorter in the retracted state than in the extended state.

A9. The system of any of embodiments A1-A8, wherein the toroidal component comprises an elastomeric material such as silicone, urethane, latex, butyl rubber, neoprene, vinyl, fluoroelastomer, or an elastomeric foam.

A10. The system of any of embodiments A1-A9, wherein the toroidal component is elastically stable in either the retracted or extended state.

A11. The system of any of embodiments A1-A10, wherein the toroidal component is sized and shaped to be inserted, at least partially, into an ear canal.

A12. The system of any of embodiments A1-A11, wherein the fluid disposed within the interior volume of the toroidal component is a fluid suspension comprising a plurality of gas-filled spheres dispersed in a liquid or gas.

A13. The system of any of embodiments A1-A11, wherein the fluid disposed within the interior volume of the toroidal component is a fluid suspension comprising a plurality of solid particles dispersed in a liquid or gas.

B1. A method for occluding a duct or orifice, the method comprising:
   inserting, at least partially, a toroidal component into the duct or orifice while the toroidal component is in a retracted state, the toroidal component enclosing an interior volume that contains a fluid; and
   transitioning the toroidal component from the retracted state to an extended state, the step of transitioning the toroidal component to the extended state causing the toroidal component to extend farther into the duct or orifice;
   wherein:
      when the toroidal component is in the extended state:
         the interior volume is disposed between an inner surface and an outer surface of the toroidal component;
         a distal portion of the toroidal component that defines a distal tip is configured to extend in a distal direction into an entrance of the duct or orifice; and
         a proximal portion of the toroidal component defining a proximal end of the toroidal component is configured to extend in a proximal direction opposite the distal direction; and when the toroidal component is in the retracted state, a portion of the inner surface extends proximally beyond the proximal end of the toroidal component.

B2. The method of embodiment B1, wherein the toroidal component has a central channel, the portion of the inner surface being disposed within the central channel when the toroidal component is in the extended state.

B3. The method of embodiment B2, wherein a second component extends at least partially within the central channel and engages the portion of the inner surface.

B4. The method of embodiment B3, wherein the portion of the inner surface comprises a structure to which the second component snap-fits and engages.

B5. The method of any of embodiments B3-B4, wherein the second component comprises an air cavity and a vent, wherein:
  when the toroidal component is in the retracted state, the vent allows air to travel between the air cavity and an external environment; and
  when the toroidal component is in the extended state, the vent is disposed within the central channel.

B6. The method of embodiment B5, wherein the second component has an opening at its distal end that communicates with the central channel of the toroidal component such that, when the system is in the extended state, the central channel of the toroidal component and the air cavity of the second component form a combined sealed air volume that is larger than a volume of the central channel alone, the larger combined sealed air volume reducing an amplitude of pressure changes in response to a given axial displacement of the system within the duct or orifice.

B7. The method of any of embodiments B3-B6, wherein upon inserting the toroidal component into the duct or orifice while the system is in the retracted state, pressing the second component in the distal direction causes the toroidal component to transition from the retracted state to the extended state.

B8. The method of any of embodiments B2-B7, wherein, when the toroidal component is in the retracted state, the distal portion of the toroidal component is drawn proximally into the central channel, such that a distal extent of the toroidal component measured from the proximal end to a distalmost portion of the toroidal component is shorter in the retracted state than in the extended state.

B9. The method of any of embodiments B1-B8, wherein the toroidal component comprises an elastomeric material such as silicone, urethane, latex, butyl rubber, neoprene, vinyl, fluoroelastomer, or an elastomeric foam.

B10. The method of any of embodiments B1-B9, wherein the toroidal component is elastically stable in either the retracted or extended state.

B11. The method of any of embodiments B1-B10, wherein the duct or orifice is an ear canal.

B12. The method of any of embodiments B1-B11, wherein the fluid disposed within the interior volume of the toroidal component is a fluid suspension comprising a plurality of gas-filled spheres dispersed in a liquid or gas.

B13. The method of any of embodiments B1-B11, wherein the fluid disposed within the interior volume of the toroidal component is a fluid suspension comprising a plurality of solid particles dispersed in a liquid or gas.

C1. A device for attenuating sound passing through a duct or orifice, the device comprising:
  a body sized and shaped to be inserted, at least partially, into a duct or orifice;
  the body comprising an interior volume that contains a fluid suspension;
  wherein the fluid suspension comprises a plurality of gas-filled spheres dispersed in an interstitial fluid, the gas-filled spheres increasing an acoustic attenuation of the fluid suspension relative to the interstitial fluid alone.

C2. The device of embodiment C1, wherein one or more of the spheres comprises a shell having a thickness less than 5 microns and an elastic modulus that is between 1 and 5 GPa.

C3. The device of any of embodiments C1-C2, wherein, when the device is at atmospheric pressure, the plurality of spheres occupies a volume fraction of the fluid suspension that is between 0.4 and 0.7.

C4. The device of any of embodiments C1-C3, wherein one or more of the spheres are filled with a gas having a molecular weight of at least 100 g/mol.

C5. The device of any of embodiments C1-C4, wherein the interstitial fluid is a liquid, emulsion, or solution, and the plurality of spheres increases viscosity and compressibility of the fluid suspension relative to the interstitial fluid alone.

C6. The device of any of embodiments C1-C4, wherein the interstitial fluid is a gas, and the plurality of spheres flows as a dry powder such that the fluid suspension has non-linear viscosity and acoustic properties.

C7. The device of any of embodiments C1-C6, wherein the device is sized and shaped to be inserted at least partially into an ear canal.

C8. The device of any of embodiments C1-C7, wherein the device comprises a toroidal component that encloses the interior volume containing the fluid suspension, the toroidal component having an extended state and a retracted state;
  wherein:
    when the toroidal component is in the extended state:
      the interior volume is disposed between an inner surface and an outer surface of the toroidal component;
      a distal portion of the toroidal component that defines a distal tip is configured to extend in a distal direction into the entrance of the duct or orifice; and
      a proximal portion of the toroidal component defining a proximal end of the toroidal component is configured to extend in a proximal direction opposite the distal direction; and
    when the toroidal component is in the retracted state, a portion of the inner surface extends proximally beyond the proximal end of the toroidal component.

D1. A method for attenuating sound passing through a duct or orifice, the method comprising:
  inserting, at least partially, into the duct or orifice a device, the device comprising an interior volume that contains a fluid suspension;
  wherein the fluid suspension comprises a plurality of gas-filled spheres dispersed in an interstitial fluid, the gas-filled spheres increasing an acoustic attenuation of the fluid suspension relative to the interstitial fluid alone.

D2. The method of embodiment D1, wherein one or more of the spheres comprises a shell having a thickness less than 5 microns and an elastic modulus that is between 1 and 5 GPa.

D3. The method of any of embodiments D1-D2, wherein, when the device is at atmospheric pressure, the plurality of spheres occupies a volume fraction of the fluid suspension that is between 0.4 and 0.7.

D4. The method of any of embodiments D1-D3, wherein one or more of the spheres are filled with a gas having a molecular weight of at least 100 g/mol.

D5. The method of any of embodiments D1-D4, wherein the interstitial fluid is a liquid, emulsion, or solution, and the plurality of spheres increases viscosity and compressibility of the fluid suspension relative to the interstitial fluid alone.

D6. The method of any of embodiments D1-D4, wherein the interstitial fluid is a gas, and the plurality of spheres flows as a dry powder such that the fluid suspension has non-linear viscosity and acoustic properties.

D7. The method of any of embodiments D1-D6, wherein the device is sized and shaped to be inserted at least partially into an ear canal.

D8. The method of any of embodiments D1-D7, wherein the device comprises a toroidal component that encloses the interior volume containing the fluid suspension, the toroidal component having an extended state and a retracted state;
wherein:
when the toroidal component is in the extended state:
the interior volume is disposed between an inner surface and an outer surface of the toroidal component;
a distal portion of the toroidal component that defines a distal tip is configured to extend in a distal direction into the entrance of the duct or orifice; and
a proximal portion of the toroidal component defining a proximal end of the toroidal component is configured to extend in a proximal direction opposite the distal direction; and
when the toroidal component is in the retracted state, a portion of the inner surface extends proximally beyond the proximal end of the toroidal component.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations are not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A device for attenuating sound passing through a duct or orifice, the device comprising:
a body sized and shaped to be inserted, at least partially, into a duct or orifice; and
the body comprising an interior volume that contains a fluid suspension, wherein the fluid suspension comprises a plurality of gas-filled spheres dispersed in an interstitial fluid, the gas-filled spheres increasing an acoustic attenuation of the fluid suspension relative to the interstitial fluid alone;
wherein the interstitial fluid is at least one of a liquid, emulsion, or solution, and the plurality of gas-filled spheres increases viscosity and compressibility of the fluid suspension relative to the interstitial fluid alone.

2. The device of claim 1, wherein one or more of the plurality of gas-filled spheres comprises a shell having a thickness less than 5 microns and an elastic modulus that is between 1 and 5 GPa.

3. The device of claim 1, wherein, when the device is at atmospheric pressure, the plurality of gas-filled spheres occupies a volume fraction of the fluid suspension that is between 0.4 and 0.7.

4. The device of claim 1, wherein one or more of the plurality of gas-filled spheres are filled with a gas having a molecular weight of at least 100 g/mol.

5. The device of claim 1, wherein the interstitial fluid is a gas, and the plurality of spheres flows as a dry powder such that the fluid suspension has non-linear viscosity and acoustic properties.

6. The device of claim 1, wherein the device is sized and shaped to be inserted at least partially into an ear canal.

7. The device of claim 1, wherein the device comprises a toroidal component that encloses the interior volume containing the fluid suspension, the toroidal component having an extended state and a retracted state;
wherein:
when the toroidal component is in the extended state:
the interior volume is disposed between an inner surface and an outer surface of the toroidal component;
a distal portion of the toroidal component that defines a distal tip is configured to extend in a distal direction into the entrance of the duct or orifice; and
a proximal portion of the toroidal component defining a proximal end of the toroidal component is configured to extend in a proximal direction opposite the distal direction;
when the toroidal component is in the retracted state, a portion of the inner surface extends proximally beyond the proximal end of the toroidal component; and
the toroidal component is configured such that inserting the toroidal component into the ear canal while the toroidal component is in the retracted state and then transitioning the toroidal component to the extended state within the ear canal causes the distal tip to extend a distance within the ear canal such that the distal tip is disposed within an inner portion of the ear canal that is surrounded by bony tissue.

8. A method for attenuating sound passing through a duct or orifice, the method comprising:
inserting, at least partially, into the duct or orifice a device, the device comprising an interior volume that contains a fluid suspension, wherein the fluid suspension comprises a plurality of gas-filled spheres dispersed in an interstitial fluid, the gas-filled spheres increasing an acoustic attenuation of the fluid suspension relative to the interstitial fluid alone;
wherein the interstitial fluid is at least one of a liquid, emulsion, or solution, and the plurality of gas-filled spheres increases viscosity and compressibility of the fluid suspension relative to the interstitial fluid alone.

9. The method of claim 8, wherein one or more of the plurality of gas-filled spheres comprises a shell having a thickness less than 5 microns and an elastic modulus that is between 1 and 5 GPa.

10. The method of claim 9, wherein, when the device is at atmospheric pressure, the plurality of gas-filled spheres occupies a volume fraction of the fluid suspension that is between 0.4 and 0.7.

11. The method of claim 8, wherein one or more of the plurality of gas-filled spheres are filled with a gas having a molecular weight of at least 100 g/mol.

12. The method of claim 8, wherein the interstitial fluid is a gas, and the plurality of gas-filled spheres flows as a dry powder such that the fluid suspension has non-linear viscosity and acoustic properties.

13. The method of claim 8, wherein the device is sized and shaped to be inserted at least partially into an ear canal.

14. The method of claim 8, wherein the device comprises a toroidal component that encloses the interior volume containing the fluid suspension, the toroidal component having an extended state and a retracted state;
wherein:
when the toroidal component is in the extended state:
the interior volume is disposed between an inner surface and an outer surface of the toroidal component;
a distal portion of the toroidal component that defines a distal tip is configured to extend in a distal direction into the entrance of the duct or orifice; and
a proximal portion of the toroidal component defining a proximal end of the toroidal component is configured to extend in a proximal direction opposite the distal direction;
when the toroidal component is in the retracted state, a portion of the inner surface extends proximally beyond the proximal end of the toroidal component; and
the toroidal component is configured such that inserting the toroidal component into the ear canal while the toroidal component is in the retracted state and then transitioning the toroidal component to the extended state within the ear canal causes the distal tip to extend a distance within the ear canal such that the distal tip is disposed within an inner portion of the ear canal that is surrounded by bony tissue.

* * * * *